United States Patent [19]
Hensen et al.

[11] Patent Number: 5,883,068
[45] Date of Patent: Mar. 16, 1999

[54] PUMPABLE WATER-CONTAINING SURFACTANT CONCENTRATES

[75] Inventors: Hermann Hensen, Haan; Renate Lindner, Hilden; Joerg Kahre, Monheim; Werner Seipel, Hilden, all of Germany

[73] Assignee: Henkel Kommanditgesellschaft auf Aktien, Duesseldorf, Germany

[21] Appl. No.: 817,046

[22] PCT Filed: Sep. 25, 1995

[86] PCT No.: PCT/EP95/03795

§ 371 Date: Apr. 4, 1997

§ 102(e) Date: Apr. 4, 1997

[87] PCT Pub. No.: WO96/10622

PCT Pub. Date: Apr. 11, 1996

[30] Foreign Application Priority Data

Oct. 4, 1994 [DE] Germany ............ 44 35 387.1

[51] Int. Cl.⁶ .................. C11D 1/72; C11D 1/831
[52] U.S. Cl. ............ 510/427; 510/424; 510/428; 510/470
[58] Field of Search ............... 510/424, 426, 510/427, 428, 470

[56] References Cited

U.S. PATENT DOCUMENTS

| | | | |
|---|---|---|---|
| 4,668,422 | 5/1987 | Malik et al. | 252/174.17 |
| 4,839,098 | 6/1989 | Wisotzki et al. | 252/557 |
| 5,015,414 | 5/1991 | Kamegai et al. | 252/545 |
| 5,108,585 | 4/1992 | Von Rybinski et al. | 209/166 |
| 5,374,716 | 12/1994 | Biermann et al. | 536/18.6 |
| 5,576,425 | 11/1996 | Hill et al. | 536/18.6 |
| 5,578,560 | 11/1996 | Giesen et al. | 510/237 |

FOREIGN PATENT DOCUMENTS

| | | |
|---|---|---|
| 0 127 580 | 12/1984 | European Pat. Off. . |
| 0 219 057 | 4/1987 | European Pat. Off. . |
| 0 250 181 | 12/1987 | European Pat. Off. . |
| 0 280 143 | 8/1988 | European Pat. Off. . |
| 0 301 298 | 2/1989 | European Pat. Off. . |
| 0 341 071 | 11/1989 | European Pat. Off. . |
| 0 358 216 | 3/1990 | European Pat. Off. . |
| 0 409 005 | 1/1991 | European Pat. Off. . |
| 0 453 238 | 10/1991 | European Pat. Off. . |
| 0 508 507 | 10/1992 | European Pat. Off. . |
| 0 572 776 | 12/1993 | European Pat. Off. . |
| 40 07 757 | of 0000 | Germany . |
| 41 39 935 | 6/1993 | Germany . |
| 42 34 487 | 4/1994 | Germany . |
| 43 11 114 | 10/1994 | Germany . |
| 90/01441 | 2/1990 | WIPO . |
| 90/03977 | 4/1990 | WIPO . |
| 91/04313 | 4/1991 | WIPO . |
| 93/25650 | 12/1993 | WIPO . |

OTHER PUBLICATIONS

Skin Care Forum, (1992) p. 1. No month available.
Seifen–Öle–Fette–Washse, 118, (1992) p. 894. No month available.
Seifen–Öle–Fette–Washse, 118, (1992) p. 905. No month available.
Rivista Italiana, 56, (1974) p. 567. No month available.
Cosm. Toil., 104, (1989) p. 105. No month available.
R. Soc. Chem. (Ind. Appl. Surf. II), 77, (1990) p. 77. No month available.
J. Am. Oil Chem. Soc., 70 (1993) p. 707. No month available.
"Kosmetische Färbemittel" der Farbstoffkommission der Deutschen Forschungsgemeinschaft, published by Verlag Chemie, Weinheim, 1984, pp. 81 to 106.

*Primary Examiner*—Paul Lieberman
*Assistant Examiner*—Necholus Ogden
*Attorney, Agent, or Firm*—Ernest G. Szoke; Wayne C. Jaeschke; Henry E. Millson, Jr.

[57] ABSTRACT

Pumpable water-containing surfactant concentrates containing alkyl glycosides, sulfosuccinates and amphoteric and/or zwitterionic surfactants, and to their use for the production of surface-active formulations.

21 Claims, No Drawings

PUMPABLE WATER-CONTAINING SURFACTANT CONCENTRATES

BACKGROUND OF THE INVENTION

1. Field of the Invention

This invention relates to pumpable water-containing surfactant concentrates containing alkyl glycosides, sulfosuccinates and amphoteric surfactants, and to their use for the production of surface-active formulations.

2. Statement of Related Art

Alkyl oligoglycosides, more particularly alkyl oligoglucosides, are nonionic surfactants which are acquiring increasing significance by virtue of their excellent detergent properties and their high ecotoxicological compatibility. The production and use of these substances have been described just recently in a number of synoptic articles, of which the articles by H. Hensen in Skin Care Forum, 1, (October 1992), D. Balzer and N. Ripke in Seifen-Öle-Fette-Wachse 118, 894 (1992) and B. Brancq in Seifen-Öle-Fette-Wachse 118, 905 (1992) are cited as examples.

In some respects, however, the use of alkyl oligoglucosides is attended by problems. For example, it is not possible to produce pumpable water-containing concentrates with a solids content above 40% by weight without the sugar component undergoing partial decomposition in the course of the concentration process. The glycosides share this property with most anionic surfactants which form a viscous gel phase above an active substance content of around 35% by weight. In addition, alkyl oligoglucosides tend to crystallize during storage at low temperatures which significantly complicates their subsequent use.

Numerous surfactant mixtures containing alkyl glycosides as one component are already known from the prior art but do not solve any of the problems mentioned above.

Thus, mixtures of short-chain alkyl glycosides with sulfosuccinates for the production of hair shampoos and baby foam baths are described, for example, by G. Proserpio et al. in Rivista Italiana 56, 567 (1974). Mixtures of alkyl glycosides with sulfosuccinates for use as collectors in flotation are known from EP-A 0 219 057 (Henkel). EP-A 0 280 143 (Henkel) describes manual dishwashing detergents containing dioctyl sulfosuccinates. Mild surfactant mixtures containing sulfosuccinates, preferably monoalkyl sulfosuccinates, are claimed very broadly in EP-A 0 358 216 (Kao) and in WO 90/01441 (Henkel Corp.). The use of alkyl glycosides for regulating the viscosity of sulfosuccinate pastes is proposed in WO 91/04313 (Henkel Corp.) and in DE-A 4 007 757 (Henkel). In addition, liquid cleaning formulations which may contain alkyl glycosides and sulfosuccinates as components are known from DE-A 4 139 935 (Kao) and from EP-A 0 572 776 (Hüls).

Finally, EP-A 0 453 238 (Unilever) claims mild shampoos containing anionic surfactants (for example fatty alcohol ethersulfates and sulfosuccinates), amphoteric surfactants (for example betaines) and nonionic surfactants (for example fatty alcohol polyglycol ethers and alkyl glycosides). However, the solids content of the mixtures is well below 20% by weight. In addition, combinations of alkyl glycosides, sulfosuccinates and amphoteric surfactants are not expressly mentioned.

Combinations of alkyl glycosides with amphoteric surfactants of the betaine type are described, for example, in the following documents: US 4,668,422 (Henkel Corp.), EP-A 0 250 181 (Helene Curtis), EP-A 0 341 071 (Unilever), EP-A 0 508 507 (Berol Nobel) and DE-A 4 234 487 and DE-A 4 311 114 (Henkel).

There is a need in the market for concentrated surfactant mixtures based on alkyl and/or alkenyl oligoglucosides which are flowable and pumpable, despite a solids content above 30% by weight and preferably from around 40 to 45% by weight, and show a significantly reduced tendency towards crystallization, i.e. improved stability in storage. Since surfactant compounds of the type in question are mainly used in the cosmetics field, skin-cosmetic or rather dermatological compatibility is also of paramount importance.

Surfactant concentrates are a particularly convenient commercial formulation for manufacturers and users alike because they have been minimized in regard to their water content and hence incur lower transport and storage costs. Nevertheless, it is desirable that surfactant concentrates should have a sufficiently high viscosity for use in the end products, which are of course heavily diluted and have a solids content of 20 to 30% by weight, and should be readily thickenable using known additives.

Accordingly, the complex problem addressed by the present invention was to provide pumpable water-containing surfactant concentrates with high skin cosmetic compatibility based on alkyl and/or alkenyl oligoglycosides which would be distinguished by high stability in storage, would have a Brookfield viscosity of at most 10,000 mPa.s and a solids content of 30 to 50% by weight and would readily lend themselves to thickening to a viscosity of at least 2,000 mPa.s on incorporation in cosmetic formulations with a water content of at least 50% by weight.

Description of the Invention

The present invention relates to pumpable water-containing surfactant concentrates with a solids content of 30 to 50% by weight containing (a) alkyl and/or alkenyl oligoglycosides,
(b) sulfosuccinates and
(c) amphoteric or zwitterionic surfactants, preferably of the betaine type.

It has surprisingly been found that the surfactant concentrates according to the invention show excellent dermatological compatibility and very good stability in storage, even at low temperatures. In particular, the formation of crystals, as known from water-containing alkyl glucoside pastes, is reliably avoided. The present invention also includes the observation that the surfactant concentrates have the necessarily low viscosity of less than 10,000 mPa.s and preferably 3,000 to 7,500 mPa.s (as determined by the Brookfield method), but can readily be thickened to a viscosity of at least 2,000 mPa.s in dilute water-containing formulations.

Alkyl and/or Alkenyl Oligoglycosides

Alkyl and/or alkenyl oligoglycosides are known substances and correspond to formula (I):

$$R^1O\text{---}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10. Alkyl and/or alkenyl oligoglycosides may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol having a DP of 1 to 3 are preferred.

Sulfosuccinates

Sulfosuccinates, which are also known as sulfosuccinic acid esters, are known anionic surfactants which may be obtained by the relevant methods of preparative organic chemistry. They correspond to formula (II):

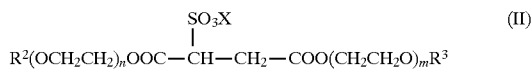

in which $R^2$ is an alkyl and/or alkenyl radical containing 6 to 22 carbon atoms, $R^3$ has the same meaning as $R^1$ or X, m and n independently of one another are 0 or numbers of 1 to 10 and X is an alkali metal or alkaline earth metal, ammonium, alkylammonium, alkanolammonium or glucammonium.

They are normally produced from maleic acid and preferably from maleic anhydride which, in the first step, is esterified with optionally ethoxylated primary alcohols. The ratio of monoester to diester can be adjusted at this stage by varying the quantity of alcohol and the temperature. The second step comprises the addition of bisulfite which is normally carried out in methanol as solvent. Fairly recent overviews of the production and use of sulfosuccinates have been published, for example, by T. Schoenberg in Cosm. Toil. 104, 105 (1989), J. A. Milne in R. Soc. Chem. (Ind. Appl. Surf. II) 77, 77 (1990) and by W. Hreczuch et al. in J. Am. Oil. Chem. Soc. 70, 707 (1993).

Typical examples are sulfosuccinic acid monoesters and/or diesters in the form of their sodium salts derived from fatty alcohols containing 8 to 18 and preferably 8 to 10 or 12 to 14 carbon atoms. The fatty alcohols may be etherified with, on average, 1 to 10 and preferably 1 to 5 moles of ethylene oxide and may have both a conventional homolog distribution and, preferably, a narrow homolog distribution. Di-n-octyl sulfosuccinate and monolauryl-3EO-sulfosuccinate in the form of their sodium salts are mentioned as examples.

Amphoteric or Zwitterionic Surfactants

Typical examples of amphoteric or zwitterionic surfactants are alkyl betaines, alkyl amidobetaines, aminopropionates, aminoglycinates, imidazolinium betaines and sulfobetaines.

In one particularly preferred embodiment of the invention, condensation products of fatty acid amidoamines with halocarboxylic acid salts which correspond to formula (III):

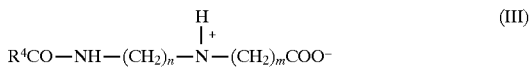

where $R^4CO$ is a saturated and/or unsaturated aliphatic acyl radical containing 6 to 22 and preferably 12 to 18 carbon atoms and n and m independently of one another are numbers of 1 to 3, are used as amphoteric surfactants.

Typical examples are condensation products of sodium chloroacetate with amidoamides of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid, and erucic acid and the technical mixtures thereof obtained, for example, in the pressure hydrolysis of natural fats and oils, in the reduction of aldehydes from Roelen's oxosynthesis or in the dimerization of unsaturated fatty acids.

Condensation products of $C_{12/14}$ or $C_{8/18}$ coconut oil fatty acid amido-ethylene amine or propylene amine with sodium chloroacetate are preferred.

The surfactant concentrates according to the invention may contain components (a), (b) and (c) in quantities of 25 to 50% by weight and preferably 30 to 40% by weight, with the proviso that the figures always add up to 100% by weight. In addition, the mixtures have a water content of at least 50% by weight and at most 70% by weight and preferably in the range from 55 to 60% by weight.

COMMERCIAL APPLICATIONS

The water-containing surfactant concentrates according to the invention have a solids content of 30 to 50% by weight. They are stable in storage, do not show any tendency to crystallize, have a viscosity of less than 10,000 mPa.s and, accordingly, are pumpable. In dilute water-containing formulations, they can readily be rethickened and show excellent dermatological compatibility. If the surfactant concentrates already contain a thickener, there may often be no need at all to add other thickeners, preferably narrow-range fatty alcohol polyglycol ethers, to the cosmetic formulations because the required viscosity is automatically established. Accordingly, the present invention also relates to the use of the surfactant concentrates according to the invention for the production of surface-active formulations, such as for example dishwashing detergents and, in particular, skin-care and hair-care formulations.

Skin-Care and Hair-Care Formulations

The skin-care and hair-care formulations may contain further surfactants compatible with the other ingredients in small quantities. Typical examples are fatty alcohol polyglycol ethersulfates, monoglyceride sulfates, ether carboxylic acids, fatty acid isethionates, fatty acid sarcosinates, fatty acid taurides and/or protein hydrolyzates or condensates thereof with fatty acids of animal or preferably vegetable origin.

In addition to the surfactants already mentioned, skin-care formulations, such as creams, lotions and the like, generally contain oils, emulsifiers, fats and waxes, stabilizers and also superfatting agents, thickeners, biogenic agents, film formers, preservatives, dyes and fragrances.

In addition to the surfactants already mentioned, hair-care formulations, such as for example hair shampoos, hair lotions, foam baths and the like, may contain emulsifiers, superfatting agents, thickeners, biogenic agents, film formers, preservatives, dyes and fragrances as further auxiliaries and additives.

Suitable oil components are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more particularly 2-ethylhexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes, Guerbet carbonates and/or dialkyl ethers.

Suitable emulsifiers are both known w/o and o/w emulsifiers such as, for example, hydrogenated and ethoxylated castor oil, polyglycerol fatty acid esters or polyglycerol polyricinoleates.

Typical examples of fats are glycerides while suitable waxes include inter alia beeswax, paraffin wax or microwaxes, optionally in combination with hydrophilic waxes, for example cetostearyl alcohol.

Suitable stabilizers are metal salts of fatty acids such as, for example, magnesium, aluminium and/or zinc stearate.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, narrow-range fatty alcohol ethoxylates or alkyl oligoglucosides and electrolytes, such as sodium chloride and ammonium chloride.

In the context of the invention, biogenic agents are, for example, plant extracts and vitamin complexes.

Typical film formers are, for example, chitosan, microcrystalline chitosan or quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and also fatty acid monoglycol esters.

The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be from 1 to 50% by weight and is preferably from 5 to 40% by weight while the nonaqueous component ("active substance content") may amount to between 20 and 80% by weight and preferably to between 30 and 70% by weight, based on the formulation. The formulations may be produced in known manner, i.e. for example by hot, cold, hot-hot/cold or PIT emulsification. These are all purely mechanical processes in which no chemical reaction takes place.

The following Examples are intended to illustrate the invention without limiting it in any way.

EXAMPLES

I. Testing of the Concentrates

The viscosity of the following mixtures was determined by the Brookfield method (20° C., spindle 4, 10 r.p.m.). The stability of the mixtures was visually evaluated after storage for 4 weeks at 5° C. The symbols used have the following meanings:

+++= clear solution, no crystallization

++= some crystallization

+= distinct crystallization

−= parts of the solution completely crystallized

\* = hazy product, unstable, phase separation

The compositions and the viscosity and stability data are set out in Tables 1 and 2. The figures relating to the compositions of the mixtures (in % by weight) are based on the solids content of the components. All the mixtures were used with a water content of 55% by weight (pH value=5.3).

An explanation of the trade names is given in Table 4.

TABLE 1 and 2

Suractant concentrates according to the invention and comparison mixtures

| Components | 1 | 2 | 3 | 4 | 5 |
|---|---|---|---|---|---|
| Plantaren ® 1200 | 36.0 | — | — | — | — |
| Plantaren ® 2000 | — | 37.0 | 37.0 | 37.5 | 36.0 |
| Texapon ® SB 3 | 30.0 | 30.0 | 30.0 | 30.0 | 30.0 |
| Dehyton ® G | 30.0 | 30.0 | 30.0 | 30.0 | 30.0 |
| Arlypon ® F | 1.0 | 1.0 | 0.5 | — | 1.5 |
| Preservative | 0.1 | 0.1 | 0.1 | 0.1 | 0.1 |
| Lactic acid 85% | 2.9 | 1.9 | 2.4 | 2.4 | 2.4 |
| Viscosity [mPas] | 7100 | 4600 | 4050 | 3400 | 4500 |
| Stability | +++ | +++ | +++ | +++ | +++ |

| Components | C1 | C2 | C3 | C4 | C5 |
|---|---|---|---|---|---|
| Plantaren ® 1200 | 50.0 | — | — | 50.0 | 50.0 |
| Plantaren ® 2000 | — | 50.0 | — | — | — |
| Texapon ® SB 3 | 46.0 | 46.0 | 50.0 | 40.0 | 6.0 |
| Dehyton ® G | — | — | 46.0 | 6.0 | 40.0 |
| Arlypon ® F | 1.0 | 1.0 | 1.0 | 1.0 | 1.0 |
| Preservative | 0.1 | 0.1 | 0.1 | 0.1 | 0.1 |
| Lactic acid 85% | 2.9 | 2.9 | 2.9 | 2.9 | 2.9 |
| Viscosity [mPas] | 14000 | 12000 | 5500 | 9500 | 9500 |
| Stability | − | — | \* | ++ | + |

II. Testing of the Dilute Ready-To-Use Formulations

Concentrates 1 to 5 according to the invention and comparison mixtures C1 to C5 were used in the formulation of a dilute cosmetic skin lotion:

Surfactant concentrate (water-free) 10.0% by weight
Dehyton® K 5.0% by weight
Lamepon® S 2.5% by weight
Euperlan® PK 900 1.5% by weight
Cetiol® HE 1.0% by weight
Lamesoft® LMG 2.5% by weight
Dye 1.0% by weight
Preservative 0.1% by weight
Water 76.4% by weight The results are set out in Table 3

TABLE 3

Viscosity in the in-use concentration

| Ex. | pH Value | Viscosity mPas | Viscosity on addition of 1% by weight Arlypon ® F mPas |
|---|---|---|---|
| 1 | 5.3 | 4450 | |
| 2 | 5.2 | 4000 | |
| 3 | 5.3 | 4200 | |
| 4 | 5.4 | 4300 | |
| 5 | 5.3 | 4400 | |
| C1 | 5.3 | 980 | 1200 |
| C2 | 5.3 | 940 | 1100 |
| C3 | 5.3 | 1000 | 1220 |
| C4 | 5.3 | 980 | 1150 |
| C5 | 5.4 | 950 | 1130 |

The Examples and Comparison Examples may be summarized as follows:

Concentrated mixtures of alkyl oligoglucosides and sulfosuccinates give viscous to cuttable pastes. However, the dilute cosmetic formulations prepared from these concentrates have a very low viscosity which cannot be increased to the required value with conventional thickeners.

Concentrated mixtures of sulfosuccinates and amphoteric surfactants give low-viscosity, unstable solutions. Incorporation in the dilute cosmetic formulations results in the formation of very low-viscosity products which cannot be thickened in the required manner.

Only the surfactant concentrates according to the invention have a sufficiently low viscosity coupled with optimal storage behavior and can readily be adjusted to the required viscosity after dilution.

TABLE 4

Explanation of the trade names

| Trade Name | CTFA Registration |
|---|---|
| Arlypon ® F | Laureth-2 |
| Cetiol ® HE | PEG-7 Glyceryl Cocoate |
| Dehyton ® G | Cocoamphodiacetate |
| Dehyton ® K | Cocamidopropyl Betaine |
| Euperlan ® PK 900 | PEG-3 Distearate (and) Sodium Laureth Sulfate |
| Lamepon ® S | Potassium-Cocoyl Hydrolyzed Collagen |
| Lamesoft ® LMG | Glyceryl Laurate (and) Potassium-Cocoyl Hydrolyzed Collagen |
| Plantaren ® 1200 | Lauryl Polyglucose |
| Plantaren ® 2000 | Decyl Polyglucose |
| Texapon ® SB3 | Disodium Laureth Sulfosuccinate |

We claim:

1. A pumpable, aqueous surfactant concentrate having a solids content of from about 30 to about 50% by weight consisting of the following nonaqueous components.
   A) from about 25 to about 50% by weight of at least one alkyl or alkenyl oligoglycoside, or both;
   B) from about 25 to about 50% by weight of at least one sulfosuccinate; and
   C) from about 25 to about 50% by weight of at least one amphoteric surfactant, zwitterionic surfactant, or both;
   wherein the percentages of the above components A)–C) add up to 100% by weight and are based on the solids content of the concentrate.

2. The concentrate of claim 1 wherein component A) is at least one alkyl or alkenyl oligoglycoside of the formula:

$$R^1O\text{---}(G)_p \qquad (I)$$

in which $R^1$ is an alkyl or alkenyl radical containing 4 to 22 carbon atoms, G is a sugar unit containing 5 or 6 carbon atoms, and p is a number of 1 to 10.

3. The concentrate of claim 1 wherein component B) is at least one sulfosuccinate of the formula:

$$R^2(OCH_2CH_2)_nOOC\text{---}\underset{\underset{SO_3X}{|}}{CH}\text{---}CH_2\text{---}COO(CH_2CH_2O)_mR^3 \qquad (II)$$

in which $R^2$ is an alkyl or alkenyl radical containing 6 to 22 carbon atoms, $R^3$ is X or has the same meaning as $R^1$, m and n independently of one another are 0 or numbers of 1 to 10, and X is an alkali metal or alkaline earth metal, ammonium, alkylammonium, alkanolammonium or glucammonium ion.

4. The concentrate of claim 1 wherein component C) is at least one surfactant selected from the group consisting of alkyl betaines, alkyl amidobetaines, aminopropionates, aminoglycinates, imidazolinium betaines, and sulfobetaines.

5. The concentrate of claim 1 wherein the quantities of components A), B) and C) are each independently in the range of from about 30 to about 40% by weight.

6. The concentrate of claim 1 wherein from about 50 to about 70% by weight of water is present therein.

7. The concentrate of claim 6 wherein the water content is in the range of from about 55 to about 60% by weight.

8. The concentrate of claim 1 wherein the Bookfield viscosity is not greater than 10,000 mPa.s.

9. The concentrate of claim 8 wherein the Brookfield viscosity is in the range of from about 3,000 to about 7,500 mPa.s.

10. The concentrate of claim 2 wherein G is glucose and p is a number of from 1 to 6.

11. The concentrate of claim 10 wherein p is a number of from 1.2 to 1.4.

12. The concentrate of claim 3 wherein component B) is at least one sulfosuccinic acid monoester or diester of a fatty alcohol containing from 8 to 18 carbon atoms.

13. The concentrate of claim 12 wherein in component B), n+m=1 to 10.

14. The concentrate of claim 1 wherein component C) is an amphoteric surfactant of the formula:

$$R^4CO\text{---}NH\text{---}(CH_2)_n\text{---}\underset{\underset{H}{|}}{\overset{+}{N}}\text{---}(CH_2)_mCOO^- \qquad (III)$$

where $R^4CO$ is a saturated or unsaturated aliphatic acyl radical containing 6 to 22 carbon atoms, and n and m independently of one another are numbers of 1 to 3.

15. The concentrate of claim 14 wherein the amphoteric surfactant is the condensation product of a $C_{12/14}$ or $C_{8/18}$ coconut oil fatty acid amido-ethylene amine or propylene amine with sodium chloroacetate.

16. The concentrate of claim 1 wherein component A) is at least one alkyl or alkenyl oligoglycoside of the formula:

$$R^1O\text{---}(G)_p \qquad (I)$$

in which $R^1$ is an alkyl or alkenyl radical containing 4 to 22 carbon atoms, G is a sugar unit containing 5 or 6 carbon atoms, and p is a number of 1 to 10; component B) is at least one sulfosuccinate of the formula:

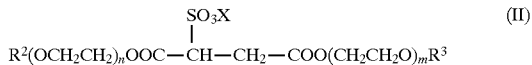  (II)

in which $R^2$ is an alkyl or alkenyl radical containing 6 to 22 carbon atoms, $R^3$ is X or has the same meaning as $R^1$, m and n independently of one another are 0 or numbers of 1 to 10, and X is an alkali metal or alkaline earth metal, ammonium, alkylammonium, alkanolammonium or glucammonium ion; and component C) is at least one surfactant selected from the group consisting of alkyl betaines, alkyl amidobetaines, aminopropionates, aminoglycinates, imidazolinium betaines, and sulfobetaines.

17. The concentrate of claim 16 wherein in component A), G is glucose and n is a number of from 1 to 6;

component B) is at least one sulfosuccinic acid monoester or diester of a fatty alcohol containing from 8 to 18 carbon atoms, and n+m=1 to 10; and component C) is an amphoteric surfactant of the formula:

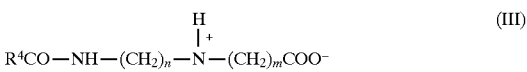  (III)

where $R^4CO$ is a saturated or unsaturated aliphatic acyl radical containing 6 to 22 carbon atoms, and n and m independently of one another are numbers of 1 to 3.

18. The concentrate of claim 16 wherein the quantities of components A), B) and C) are each independently in the range of from about 30 to about 40% by weight.

19. In a dilute cosmetic formulation, the improvement wherein a surfactant effective quantity of the composition of claim 1 is present therein.

20. The cosmetic formulation of claim 19 wherein the formulation is a skin-care formulation.

21. The cosmetic formulation of claim 19 wherein the formulation is a hair-care formulation.

* * * * *